United States Patent
Chan et al.

(10) Patent No.: US 7,938,821 B2
(45) Date of Patent: *May 10, 2011

(54) APPARATUS AND METHOD FOR ADJUSTABLE FRACTIONAL OPTICAL DERMATOLOGICAL TREATMENT

(75) Inventors: Kin F. Chan, San Jose, CA (US);
George Frangineas, Fremont, CA (US);
David Dewey, Sunnyvale, CA (US);
Leonard C. DeBenedictis, Palo Alto, CA (US)

(73) Assignee: Reliant Technologies, Inc., Hayward, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 11/777,965

(22) Filed: Jul. 13, 2007

(65) Prior Publication Data
US 2008/0015556 A1 Jan. 17, 2008

Related U.S. Application Data

(60) Provisional application No. 60/939,088, filed on May 20, 2007, provisional application No. 60/807,341, filed on Jul. 13, 2006.

(51) Int. Cl.
*A61B 18/20* (2006.01)
(52) U.S. Cl. ............ 606/9; 606/3; 606/10; 606/17; 607/88; 607/89
(58) Field of Classification Search ............ 606/3, 9–18; 607/88–91; 128/898
See application file for complete search history.

(56) References Cited

U.S. PATENT DOCUMENTS

| 4,289,378 A | 9/1981 | Remy et al. |
| 4,976,709 A | 12/1990 | Sand |

(Continued)

FOREIGN PATENT DOCUMENTS

WO     WO 00/53261 A1    9/2000

(Continued)

OTHER PUBLICATIONS

PCT International Search Report and Written Opinion, PCT/US07/16013, Feb. 6, 2008, 7 pages.

(Continued)

*Primary Examiner* — Ahmed M Farah
(74) *Attorney, Agent, or Firm* — Wood, Herron & Evans, LLP

(57) ABSTRACT

A fractional treatment system can be configured with a laser wavelength that is selected such that absorption of the laser wavelength within the tissue increases as the tissue is heated by the laser (e.g., 1390-1425 nm). Desirably, the laser wavelength is primarily absorbed within a treated region of skin by water and has a thermally adjusted absorption coefficient within the range of about 8 cm$^{-1}$ to about 30 cm$^{-1}$. An adjustable mechanism can be used to adjust the beam shape, beam numerical aperture, beam focus depth, and/or beam size to affect the treatment depth and or the character of the resulting lesions. The system may be designed to be switchable between a treatment mode that is semi-ablative and a treatment mode that is not semi-ablative. Adjustment of these parameters can improve the efficiency and efficacy of treatment. Illustrative examples of adjustable mechanisms include a set of spacers of different lengths, a rotatable turret with lens elements of different focal distances, an optical zoom lens, and a mechanical adjustment apparatus for adjusting the spacing between two optical lens elements.

36 Claims, 13 Drawing Sheets

U.S. PATENT DOCUMENTS

| | | | | |
|---|---|---|---|---|
| 5,143,063 | A | 9/1992 | Fellner | |
| 5,364,390 | A | 11/1994 | Taboada et al. | |
| 5,507,790 | A | 4/1996 | Weiss | |
| 5,558,666 | A | 9/1996 | Dewey et al. | |
| 5,810,801 | A | 9/1998 | Anderson et al. | |
| 5,836,939 | A | 11/1998 | Negus et al. | |
| 5,860,967 | A * | 1/1999 | Zavislan et al. | 606/9 |
| 5,885,211 | A | 3/1999 | Eppstein et al. | |
| 6,050,990 | A * | 4/2000 | Tankovich et al. | 606/9 |
| 6,267,779 | B1 | 7/2001 | Gerdes | |
| 6,352,502 | B1 | 3/2002 | Chaiken et al. | |
| 6,387,089 | B1 | 5/2002 | Kreindel et al. | |
| 6,406,474 | B1 | 6/2002 | Neuberger et al. | |
| 6,451,010 | B1 | 9/2002 | Angeley | |
| 6,514,278 | B1 | 2/2003 | Hibst et al. | |
| 6,529,543 | B1 | 3/2003 | Anderson et al. | |
| 6,569,157 | B1 | 5/2003 | Shain et al. | |
| 6,572,637 | B1 | 6/2003 | Yamazaki et al. | |
| 6,575,964 | B1 | 6/2003 | Hobart et al. | |
| 6,723,090 | B2 | 4/2004 | Altshuler et al. | |
| 6,997,923 | B2 * | 2/2006 | Anderson et al. | 606/9 |
| 2002/0161357 | A1 | 10/2002 | Anderson et al. | |
| 2003/0181893 | A1 | 9/2003 | Neuberger | |
| 2003/0216719 | A1 * | 11/2003 | Debenedictis et al. | 606/10 |
| 2004/0082940 | A1 | 4/2004 | Black et al. | |
| 2005/0049582 | A1 * | 3/2005 | DeBenedictis et al. | 606/9 |
| 2005/0143719 | A1 * | 6/2005 | Sink | 606/9 |
| 2005/0154380 | A1 * | 7/2005 | DeBenedictis et al. | 606/9 |
| 2005/0285928 | A1 * | 12/2005 | Broome et al. | 347/235 |
| 2008/0234669 | A1 * | 9/2008 | Kauvar | 606/9 |
| 2010/0082019 | A1 * | 4/2010 | Neev | 606/9 |

FOREIGN PATENT DOCUMENTS

| | | |
|---|---|---|
| WO | WO 2004/006793 A1 | 1/2004 |
| WO | WO 2004/007022 A1 | 1/2004 |

OTHER PUBLICATIONS

PCT International Search Report and Written Opinion, PCT/US07/73543, Feb. 5, 2008, 7 pages.

U.S. Appl. No. 11/778,012, filed Jul. 13, 2007, 42 pages.

Laufer, J. et al., "Effect of Temperature on the Optical Properties of Ex Vivo Human Dermis and Subdermis," Phys. Med. Biol., 1998, pp. 2479-2489, vol. 43.

PCT International Search Report and Written Opinion, PCT/US07/73548, Aug. 6, 2008, 6 pages.

* cited by examiner

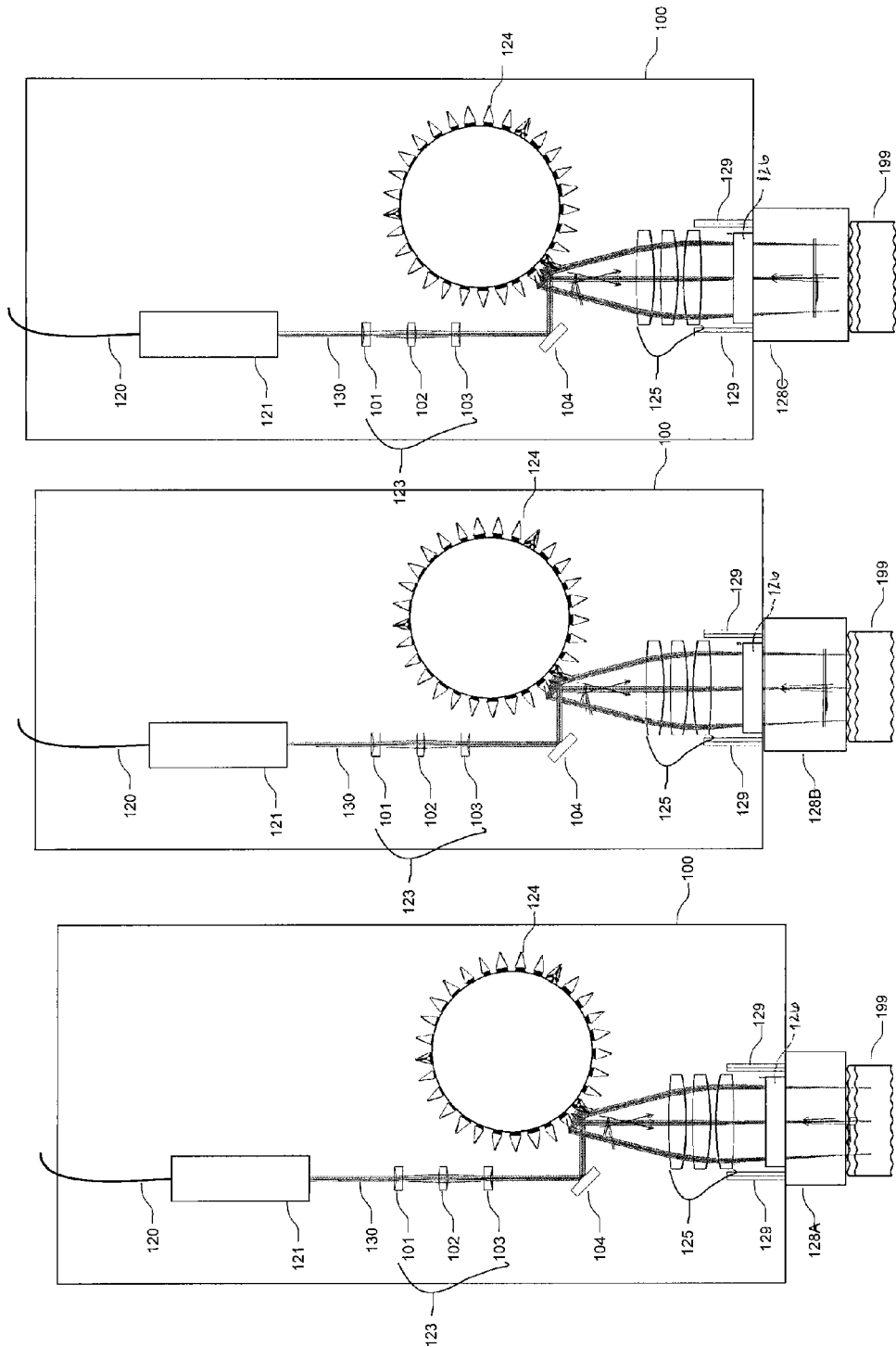

APPARATUS AND METHOD FOR ADJUSTABLE FRACTIONAL OPTICAL DERMATOLOGICAL TREATMENT

CROSS-REFERENCE TO RELATED APPLICATION

This application claims priority under 35 U.S.C. § 119(e) to U.S. Provisional Patent Application Ser. No. 60/807,341, "Apparatus and method for adjustable fractional optical dermatological treatment," by Kin F. Chan and Leonard C. DeBenedictis, filed Jul. 13, 2006; and claims priority under 35 U.S.C. § 119(e) to U.S. Provisional Patent Application Ser. No. 60/939,088, "Apparatus and method for adjustable fractional optical dermatological treatment," by Kin F. Chan, George Frangineas, Leonard C. DeBenedictis, and David Dewey, filed May 20, 2007. The subject matter of all of the foregoing is incorporated herein by reference in their entirety.

BACKGROUND OF THE INVENTION

1. Field of the Invention

The present invention relates generally to methods and apparatus for providing medical or surgical treatment using optical energy, and in particular to a method and apparatus for providing cosmetic and noncosmetic fractional treatment of tissue (e.g., skin) using optical radiation.

2. Description of the Related Art

Lasers can be used for cosmetic and noncosmetic treatment of tissue. For example, lasers are used in cosmetic dermatological procedures, such as skin resurfacing (including treatment of wrinkles), removal of pigmented lesions, treatment of vascular lesions, treatment of acne, treatment of acne scars, treatment of striae, etc.

The side effect profile of a dermatological laser treatment depends on a number of factors, such as the percentage of a skin area that is treated, the size of the treatment zones, shape of the treatment zone, and the character (e.g., ablative or nonablative, selective or nonselective, etc.) of the treatment that is delivered. Side effects can also result from variations within the patient population or the treatment environment. For example, the water content of a patient's skin can determine how deeply a water-absorbed wavelength of light penetrates into the skin. Other factors, such as the starting temperature of the skin and the temperature of the air can alter the effects of the laser on the skin and can affect the amount of pain perceived by the patient.

Fractional treatment can reduce some side effects relative to bulk treatment for a given level of treatment efficacy. The reduction in side effects is due in part to the improvement in predictability of the skin response that is possible with fractional treatment. Fractional treatment with a water-absorbed wavelength, for example, typically treats with very high local fluences that could not be tolerated in a bulk treatment. Skin can tolerate very high local fluences because tissue adjacent to each microscopic treatment region is spared and participates in the healing response of the wounded tissue. In fractional treatments, overtreatment and undertreatment typically results in a change in the size and shape of the lesion, but not a change in whether or not lesions occur. On the other hand, for bulk treatments, overtreatment may result in a lesion that scars an entire region of skin, while undertreatment may result in no lesion at all. Thus, through the use of very high local fluences, fractional treatments can reliably denature a desired portion of each illuminated region. Small variations in fractional treatment fluence or treatment conditions have less effect than corresponding variations would have in bulk treatment because fractional treatments can still reliably create clinically visible effects even if undertreated or overtreated.

Despite being more controlled than bulk treatments, fractional treatments still have unacceptable side effects that could be reduced by a device with improved control of lesion characteristics. For example, the side effect profile for many treatments is closely related to the percentage of cells at the dermal-epidermal junction ("DE junction") of a tissue portion that are killed during treatment. For this reason, it can be desirable to limit the percentage of treated tissue in a region. However, the treatment coverage percentage is also related to treatment efficacy in many treatment types. To achieve the desired efficacy while maintaining an acceptable side effect risk profile, it is desirable to have good control over the lesion dimensional characteristics, such as treatment zone width and depth.

In other fractional treatments, the side effect profile is strongly dependent on the distance to healthy tissue in the plane of the DE junction. Cells at the DE junction that are adjacent to treatment zones help to repair the damage created by the laser at the treatment zone and the time required for repairing treatment zones is strongly dependent on the size and shape of the treatment zone at the DE junction. For this reason, it is frequently desirable to create treatment zones with a small lesion width.

Treatment efficacy can be improved in many cases by reaching deeper tissue within the skin. This is particularly true, for example, when treating dermal scar tissue that frequently comprises scar tissue deep within the reticular dermis. In order to have short healing times and deep treatment zones, treatment zones with large aspect ratios are desirable for certain conditions. To control the diameter of the lesion at the DE junction and the depth of treatment, it is beneficial to have control over the treatment zone characteristics.

Another example where control over lesion characteristics would yield improved treatment results is in controlling the character of the treatment zones. For example, some fractional treatments are desirably not semiablative in order to reduce the duration and intensity of downtime and associated wound care following fractional laser treatment. If there is no reason to promote the disruption of epidermal layers, then it is desirable to maintain an intact epidermis to avoid an increased risk of infection, such as through creation of an open wound. On the other hand, for some treatments, it is desirable for the treatment to be semi-ablative. For example, a semi-ablative treatment can allow permeation of topically applied substances that promote the healing of the treated tissue. Existing laser treatment systems typically provide treatment that is either semi-ablative or not semi-ablative and do not have the capability of switching modes between semi-ablative and non-semi-ablative fractional treatments. A system with such capability is desirable so that two systems do not need to be purchased to accomplish these two goals.

Thus, there is a need for a fractional optical treatment system that allows for improved and adjustable control over fractional lesion characteristics, such as treatment zone width and depth, treatment zone aspect ratio, and/or the degree of disruptiveness of microscopic treatment zones.

SUMMARY OF THE INVENTION

The present invention overcomes many of the limitations of the prior art by increasing control over selected characteristics of fractional treatment zones. In one aspect, the inventive system comprises a fractional treatment system configured with a laser wavelength that is selected such that absorption of the laser wavelength within the tissue increases as the tissue is heated by the laser. Desirably, the laser wavelength is primarily absorbed within a treated region of skin by water and has certain additional characteristics as described in the following paragraphs.

In some embodiments of the invention, an adjustable lens group and/or discretely interchangeable optical elements are employed in a fractional treatment system. The adjustable lens group and/or discretely interchangeable optical elements can be used to adjust the fractional pattern according to the desired treatment parameters by varying the spot size at the surface of the skin, the focal depth of the optical beam below the surface of the skin, the numerical aperture of the optical beam as it enters the skin, and/or the beam cross-sectional shape at the surface of the skin. The variations in optical parameters can be performed manually or by electronic control.

In some embodiments of the invention, the fractional laser treatment system comprises a controller that is configured to switch the treatment system from a semi-ablative mode to a non-semi-ablative mode. In some embodiments, the fractional laser treatment system comprises a controller that is configured to switch the treatment system from a semi-ablative mode to a non-semi-ablative mode for a preselected pulse energy. In some embodiments, the system comprises a controller that is configured to switch the treatment system from a semi-ablative mode to a non-semi-ablative mode by adjusting an adjustable lens group and/or by exchanging interchangeable optical elements. The system can be further enhanced by selecting an appropriate wavelength, such as a wavelength in the range of about 1390 nm to about 1425 nm.

In some embodiments, the absorption of the laser wavelength in water is selected with specific characteristics. The laser wavelength can be selected, for example, such that the absorption of the laser wavelength for water is described by one or more of the following characteristics: (1) the thermally adjusted absorption coefficient is within the range of about 8 $cm^{-1}$ to about 30 $cm^{-1}$ or within the range of about 12 $cm^{-1}$ to about 27 $cm^{-1}$; (2) the graph of absorption for water at 30° C. as a function of wavelength has a slope of less than about 0.7 $(cm\,nm)^{-1}$ or a slope of about 0.3 to about 0.7 $(cm\,nm)^{-1}$ at the laser wavelength; and (3) the absorption of the laser wavelength in water increases by at least 10% as the temperature of water is increased from 30° C. to 80° C., increases by about 10% to about 24% as the temperature of water is increased from 30° C. to 80° C., or increases by about 16% to about 24% as the temperature of water is increased from 30° C. to 80° C.

In some embodiments of the invention, the laser wavelength is in the range of about 1390 nm to about 1425 nm. In some embodiments of the invention, the laser wavelength is in the range of about 1400 nm to about 1420 nm. In some embodiments of the invention, the laser wavelength is about 1410 nm. In some embodiments of the invention, the laser wavelength is in the range of about 1380 nm to about 1420 nm. In some embodiments of the invention, the laser wavelength is in the range of about 1835 nm to about 1880 nm. In some embodiments of the invention, the laser wavelength is in the range of about 1835 nm to about 1920 nm. In some embodiments of the invention, the laser wavelength is in the range of about 1880 nm to about 1900 nm.

In some embodiments of the invention, a laser diode is used as the optical source. In some embodiments of the invention, a fiber laser is used, for example a Raman-shifted ytterbium-doped fiber laser. Other lasers can be used in other embodiments.

In some embodiments of the invention, the laser creates lesions of a controlled depth within a treatment region of skin.

Other aspects of the invention include methods corresponding to the systems described above, and applications of these systems and methods.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 1A and 1B are side views.

FIG. 1C is a perspective view.

FIGS. 2A-2C are illustrations of the fractional treatment handpiece of FIG. 1A-1C depicting the use of an adjustable zoom lens in combination with a set of spacers of different lengths.

DEFINITIONS

For this patent application, the following terms are defined below.

The term "fractional treatment" describes a treatment comprising a series of treatment zones caused by a pattern of optical energy wherein the following condition is satisfied for a majority of the treatment zones: for each point within the treatment zone, the minimum lateral distance to a region of healthy tissue is approximately 0.5 mm or less and the treatment zone comprises a portion of the DE junction (i.e., comprises portions of dermal and epidermal tissue that were adjacent prior to treatment). For skin, such lateral distance measurements should be carried out in a 2-dimensional plane at the approximate depth of the DE junction. One example of a fractional treatment pattern is a discrete array of circular microscopic lesions, wherein each lesion has a diameter of approximately 1 mm (or less) and each lesion is adjacent to portions of healthy tissue. Another example of a fractional treatment pattern is a discrete array of lines of treatment where the width of each line is approximately 1 mm or less and the perimeter of each line is adjacent to portions of healthy tissue. In an ablative fractional treatment, the treatment zone includes the ablated region. So, for example, a 0.2 mm diameter ablated hole with a 0.2 mm coagulation region surrounding the ablated hole would be indicative of a fractional treatment. A 3 mm diameter ablated hole within a small ring of coagulation would not be indicative of fractional treatment.

The terms "laser wavelength," "laser diode wavelength," "wavelength of the laser," and similar variations describe the peak wavelength of the laser, for the wavelength band of interest.

Figure 5B:
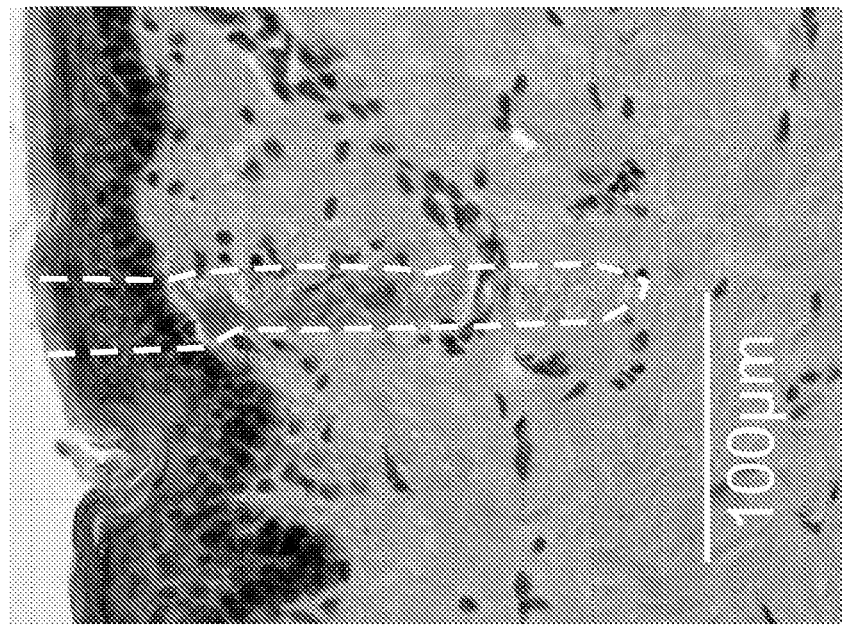
FIG. 5A-5E show histological cross sections of tissue treated according to embodiments of the invention.
Figure 5A:
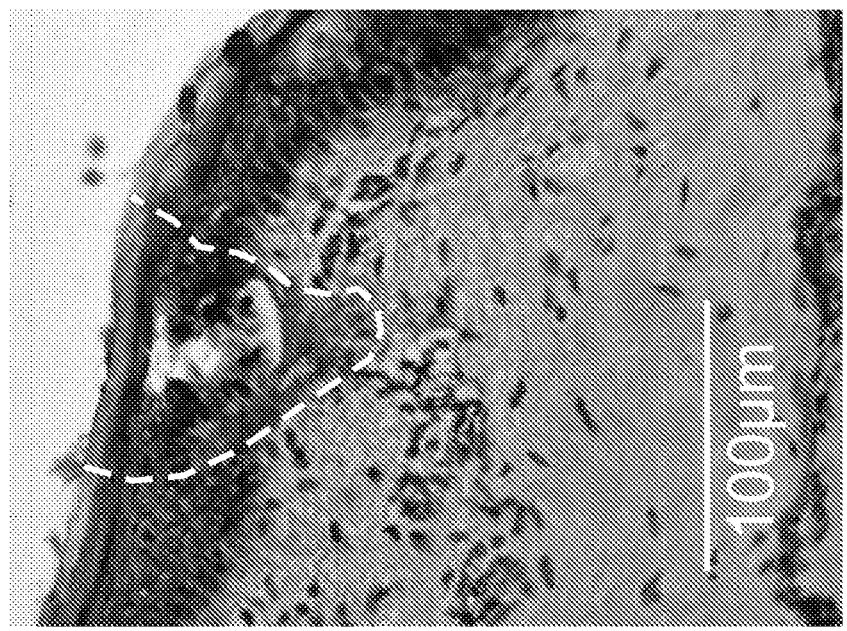
Figure 5D:
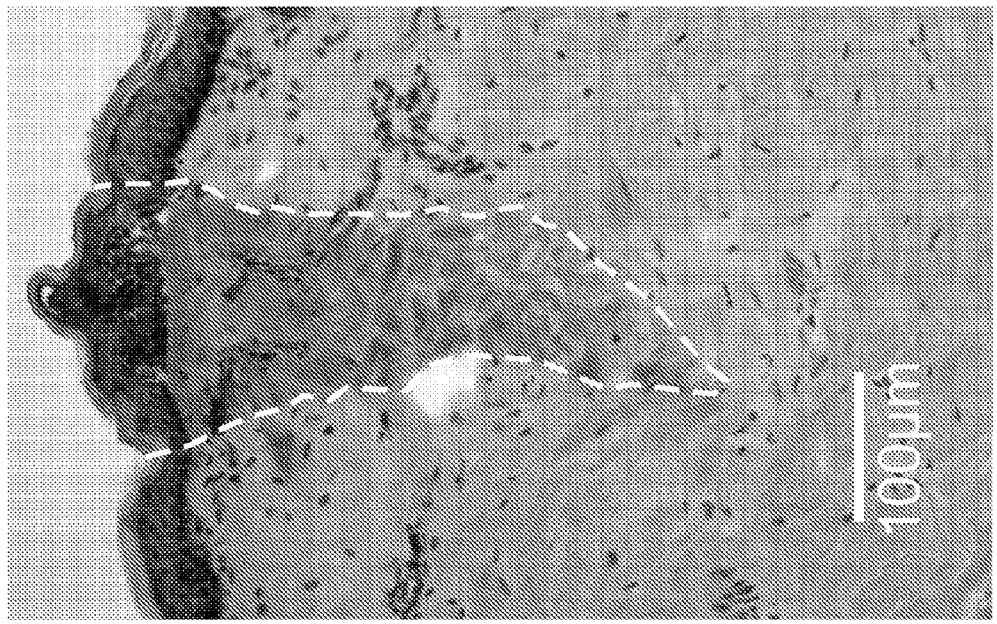
Figure 5C:
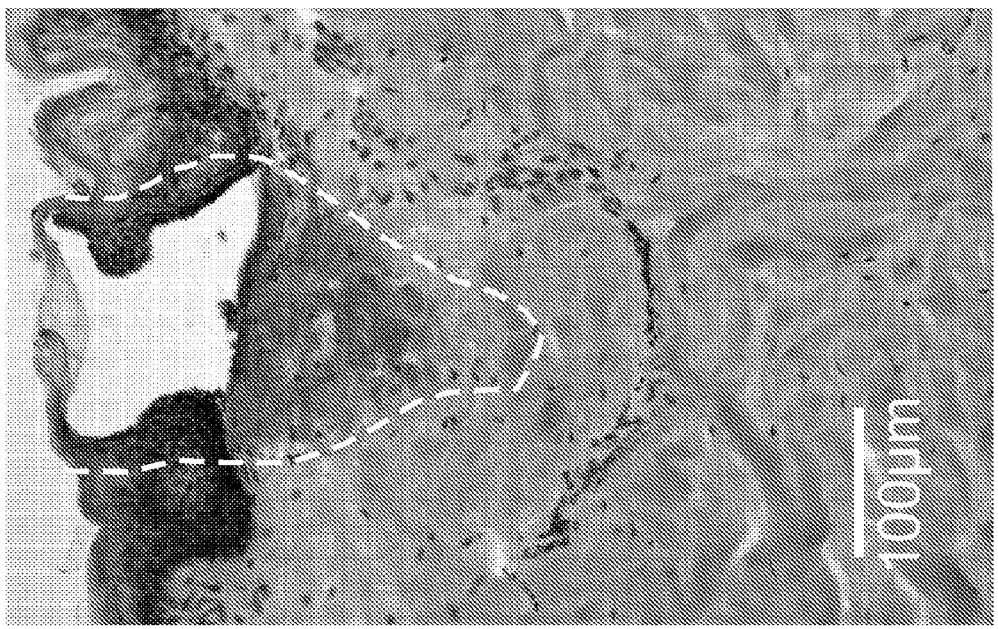
Figure 5F:
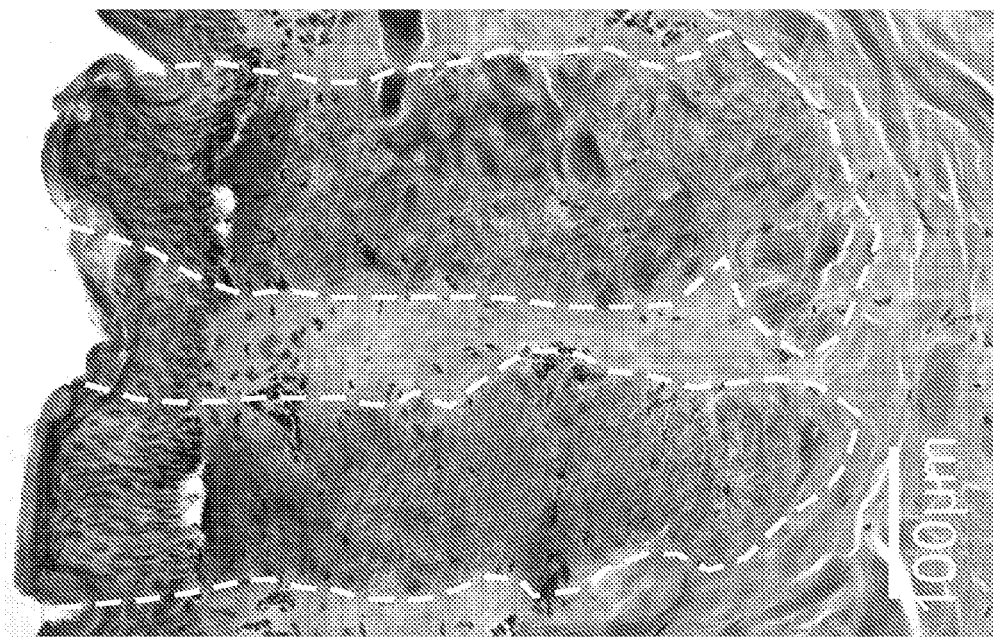
FIG. 5F shows a comparative histology of tissue treated according to an alternate method.
Figure 5E:
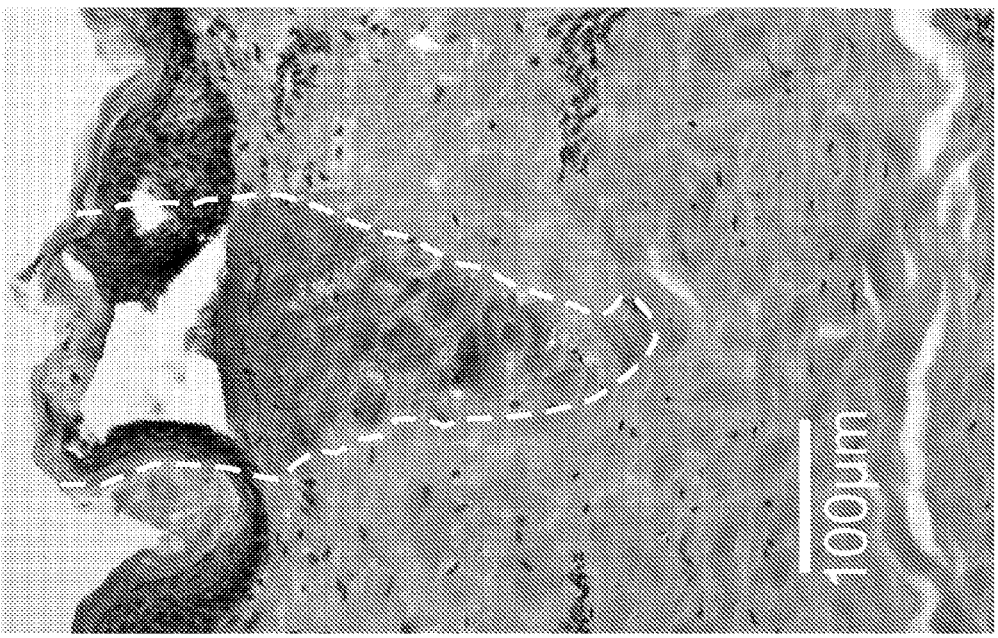

The term "semi-ablative" is an adjective that describes a treatment that significantly displaces a significant number of cells from their original location within the epidermis of a treatment zone. For example, ablative treatments are also semi-ablative. In another example, treatments that push a significant number of epidermal cells to the side beneath an intact stratum corneum would be a semi-ablative treatment. For clarity, a separation of the DE junction is not considered semi-ablative because the cells are not significantly displaced; only the adhesion between the dermal and epidermal layers has been weakened and/or broken. For clarity, a minor alteration in the skin that is not visible with an optical microscope in stained histological sections is not sufficient for classification of a treatment as semi-ablative. Semi-ablative treatments are visible in stained histological sections of the tissue following treatment when viewed under standard visible light microscopy. The lesions shown in FIGS. 5A, 5C, and 5E are illustrative examples of skin that has received semi-ablative treatments. The treatment zones shown in FIGS. 5B, 5D, and 5F are not indicative of semi-ablative treatment.

The term "thermally adjusted absorption coefficient" for a wavelength of light means the average of the absorption coefficient for water at 30° C. and the absorption coefficient of water at 80° C. for the selected wavelength.

DETAILED DESCRIPTION OF THE PREFERRED EMBODIMENTS

A fractional treatment laser system that is switchable from a semi-ablative mode to a mode that is not semi-ablative for a preselected pulse energy can be created using an adjustable lens group and/or discretely interchangeable optical elements to adjust the optical beam numerical aperture or beam size at one or more epidermal layers. Such a laser system can be created by proper selection of laser beam parameters as described above.

To demonstrate such a device, treatment zones were created by directing a laser beam onto ex vivo human skin that had been excised during one or more plastic surgery operations. Optical spot size and focus depth into the tissue sample were adjusted by adjusting the focal position of a focused laser beam relative to the tissue surface. The skin was frozen for storage and later warmed to body temperature before being treated. To approximate in vivo treatment conditions, treatment of the ex vivo tissue was performed at approximately body temperature while the sample was kept moist using saline solution. The skin was frozen and sectioned using standard histologic techniques. Staining was performed using hemotoxylin and eosin (H&E) stain to decorate features within the tissue. The results were then measured using a calibrated CCD camera mounted on a microscope. FIGS. 5A-F show sections of tissue sliced approximately perpendicular to the skin surface following laser treatments under selected exemplary conditions. The corresponding laser treatment parameters are given in Table 1.

TABLE 1

Laser beam treatment parameters for skin shown in FIGS. 5A-5F

| FIG. | Beam diameter at skin surface (to $1/e^2$ intensity point) | Treatment energy | Laser wavelength | Laser power |
|---|---|---|---|---|
| 5A | 50 µm | 1 mJ | 1410 nm | 6 W |
| 5B | 120 µm | 1 mJ | 1410 nm | 6 W |
| 5C | 130 µm | 10 mJ | 1410 nm | 4 W |
| 5D | 230 µm | 10 mJ | 1410 nm | 4 W |
| 5E | 180 µm | 10 mJ | 1410 nm | 4 W |
| 5F | 180 µm | 10 mJ | 1480 nm | 4 W |

FIGS. 5A and 5B illustrate an example of how the optical spot size at the surface of the skin can be changed to switch between a semi-ablative treatment mode and a non semi-ablative treatment mode. Both treatments are at a treatment energy of 1 mJ with a 1410 nm laser. The treatment zones resulted from different optical spot sizes at the skin surface: FIG. 5A was created using an optical spot size of 50 µm at the $1/e^2$ point of the laser treatment beam and FIG. 5B was created using an optical spot size of 120 µm at the $1/e^2$ point at the skin surface. FIG. 5A shows a treatment zone that is semi-ablative in character, while FIG. 5B shows a treatment zone that is not semi-ablative in character.

FIGS. 5C and 5D show the results of a second set of exemplary treatment conditions for which a difference in optical spot size at the skin surface can be used to create a change in the ablative character of the lesions. Both treatments are at a treatment energy of 10 mJ with a 1410 nm laser. The treatment zones resulted from different optical spot sizes at the skin surface: FIG. 5C was created using an optical spot size of 130 µm at the $1/e^2$ point at the skin surface and FIG. 5D was created using an optical spot size of 230 µm at the $1/e^2$ point at the skin surface. FIG. 5C shows a treatment zone that is semi-ablative in character, while FIG. 5D shows a treatment zone that is not semi-ablative in character.

The benefits of the increase in absorption with temperature was demonstrated as shown in ex vivo treatments at 1410 nm and 1480 nm with comparable treatment parameters. The sliced sections of tissue in FIGS. 5E and 5F show the results of ex vivo treatment at these two wavelengths with other treatment parameters held constant (10 mJ of treatment energy per treatment zone using an approximately Gaussian beam with a spot size of 180 µm at the $1/e^2$ intensity point at the skin surface). Both treatments were performed using light delivered by single mode fiber from Raman-shifted fiber lasers. Raman shifted fiber lasers are available from IPG Photonics, Inc. (Oxford, Mass.).

At 30° C., the absorption of water is approximately the same for these two wavelengths, approximately 24 $cm^{-1}$ at 1410 nm and approximately 25 $cm^{-1}$ at 1480 nm. Despite having a slightly higher absorption at 30° C., the 1480 nm light penetrated deeper than the 1410 nm wavelength. The difference in penetration was partially due to a slight difference in scattering coefficient between these wavelengths, but the difference due to scattering is small in comparison to the difference due to the dynamic absorption characteristics of the water within the treatment zone. The difference in the depth of the treatment zones created with these two wavelengths was primarily due to the difference in absorption at temperatures above 30° C. since the tissue was locally heated significantly above 30° C. by the laser treatment, particularly in the upper layers of the tissue. As the skin was heated by the laser, the absorption coefficient changed due to the change in temperature. The microscopic treatment zone that resulted from treatment with the 1410 nm laser (FIG. 5E) is semiablative and has a shallower penetration than the microscopic treatment zone that resulted from treatment with the 1480 nm laser (FIG. 5F), which was not indicative of semi-ablative treatment.

The absorption of water for the 1410 nm wavelength increases monotonicly from 30° C. to 80° C. for a total increase over this range of approximately 22%. In contrast, the 1480 nm wavelength absorption is reduced monotonicly by approximately 15% over this same temperature range. The absorption trends with temperature for these two wavelengths continue monotonicly as water is heated to at least 100° C. For these reasons, despite having approximately the same absorption coefficient at 30° C., the resulting treatment lesions are very different in character and in depth.

While having a wavelength that has an absorption in water that increases with temperature is usually desirable, it is not required to form semi-ablative treatment zones. Semi-ablative treatment zones can be created with wavelengths, such as 1480 nm, which have an absorption in water that reduces as the temperature of water increases. For example, wavelengths in the range of about 1480 nm to about 1580 nm can form semiablative treatment zones when focused to a small spot size, for example 5-80 μm, and illuminated with an optical pulse of about 1 ms of adequate fluence, for example 10-40 mJ. The exact parameters for each wavelength can be determined through experimentation.

Figure 1A:
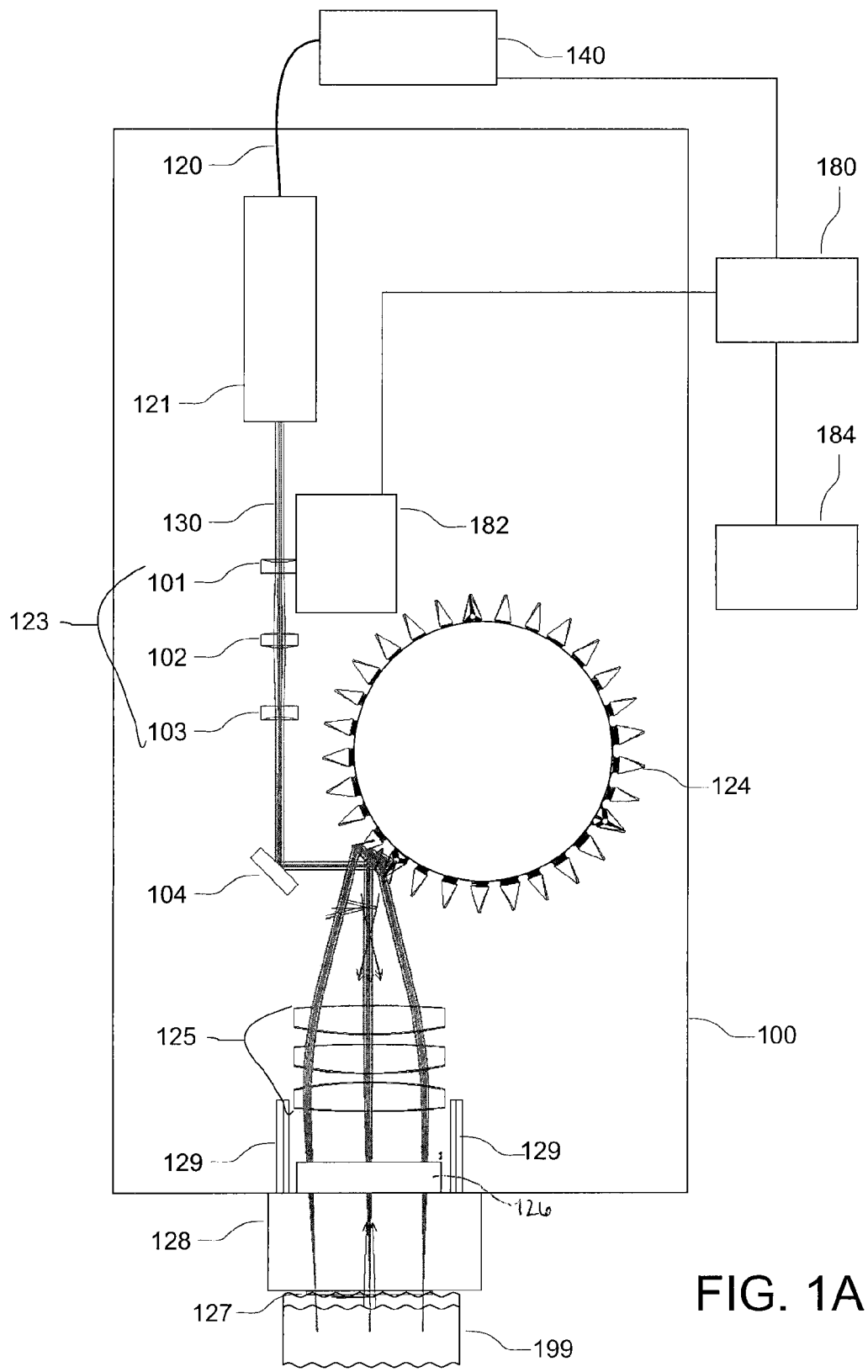
FIGS. 1A-1C are illustrations depicting different views of a fractional treatment handpiece incorporating an adjustable zoom lens and a spacer.

In some embodiments of the invention, a handpiece is used to deliver laser light to a region of skin to be treated. The handpiece illustrated in FIG. 1A comprises an optical fiber 120 that delivers optical energy from a laser source 140. The end of the optical fiber 120 is mounted in an optical collimator unit 121 to collimate the optical beam 130 emitted from the optical fiber 120. The optical beam 130 is directed towards an adjustable lens group 123 that is comprised of three lens elements 101, 102, and 103. The individual lens elements can be adjusted using a motor 182. The optical beam 130 is reflected from an optional mirror 104 into the starburst scanner wheel 124. The starburst scanner wheel 124 deflects the optical beam 130 to the output lens group 125, which focuses the optical beam 130 through the output window 126 and into the skin 199. A spacer tip 128 is mechanically registered against reference pins 129 as an aid to preserving the desired distance between the output lens group 125 and the surface of the skin 199. The output lens group may be chosen to focus the optical beam at any desired location, either in the skin 199, at the surface of the skin 199, or above the surface of the skin 199. The spacer tip 128 may optionally comprise a transparent contact plate 127.

Handpiece 100 can be moved across the skin at a constant rate in a direction into and out of the page, while the starburst scanner wheel 124 is moved at a constant rate by a motor (not pictured). This can be used to create a fractional treatment with a desired pattern. More complicated velocity feedback systems such as those employing an optical mouse chip with a contrast enhancing agent applied to the skin can be used as described, for example, in copending patent application Ser. Nos. 11/020,648, "Method and Apparatus for Monitoring and Controlling Laser-Induced Tissue Treatment" and 11/468,275, "Method And Apparatus For Monitoring And Controlling Thermally Induced Tissue Treatment," both of which are herein incorporated by reference to provide additional flexibility.

The laser source 140 comprises one or more lasers. The laser wavelength can be in the range of 1350 nm to 3000 nm. In this range, the laser is primarily and substantially absorbed within the skin by water. Since water is distributed more uniformly than chromophores within the skin, this makes treatment with a wavelength that is primarily absorbed by water less selective. Use of such a wavelength will therefore typically produce a more reproducible treatment zone than if a wavelength is used that is not substantially absorbed by water or is dependent on the specific distribution of chromophores, such as melanin or blood, within the skin.

Suitable lasers can be made at many different wavelengths and can be made from many different technologies. Diode lasers are particularly suited to some dermatological applications. For example, diode lasers are desirable because they can be manufactured inexpensively in comparison to fiber lasers. In comparison to external cavity solid state lasers, diode lasers are also cheaper and can require less maintenance to correct misalignment. Diode lasers have a broader range of accessible wavelengths than do gas lasers. Diode lasers are also easier to maintain than dye lasers. For all these reasons, it is desirable for the laser source to be a diode laser, although other sources are within the scope of the invention. Diode lasers are also very compact in comparison to other laser sources and can therefore be used more easily in treatment handpieces.

Fractional laser treatments typically use laser wavelengths that are primarily absorbed within the tissue by water because these wavelengths provide a nonselective treatment of the tissue. For such wavelengths, the absorption spectrum of light in water is important to the interaction of the light with tissue. High powered diode sources are available with wavelength outputs in the range of about 1390 to about 1425 nm, such those made in the InGaAsP/InP material system. Longer wavelengths, such as the wavelength range of about 1800 to about 1920 nm are not typically used for high power laser diodes due to the inefficiencies caused by nonradiative Auger combination of the electrons that are injected into the laser diode. Auger recombination in diode lasers is significantly worse for longer wavelengths than it is in the range of about 1390 nm to about 1425 nm. (Such longer wavelengths are currently accessable at high powers by other laser means, such as gas, external cavity solid state lasers, and fiber lasers.)

Diode lasers have a narrow wavelength spectral peak that is well defined for selected operating conditions. However, the laser diode wavelength typically shifts significantly when the temperature of the laser diode shifts. A typical diode can shift approximately 0.1 nm per degree Celcius of temperature change of the laser. The exact wavelength shift with temperature is temperature dependent and depends on device parameters such as active region material, device thermal heat path, and diode waveguide design. Diodes can be actively temperature stabilized using feedback loops with active tuning elements. Alternatively, complex device designs can be used to temperature stabilize the wavelength. However, these solutions are expensive and difficult to implement. The difficulty of controlling the wavelength of a diode is increased further because (1) the heat generated by the device depends on the output current level and (2) the temperature that is typically most important to the wavelength is the temperature of the active region of the device, rather than the temperature at an easily measured external temperature measurement point. Due to the difficulty and expense required to stabilize the wavelength of a diode laser, it is beneficial to operate in a region where the absorption spectrum in water does not change rapidly as a function of wavelength. Therefore, it is desirable to have the slope of the absorption curve at the laser wavelength as a function of wavelength to have a slope of less than 0.7 $(cm\, nm)^{-1}$ for water at 30° C. or to have a slope of about 0.3 $(cm\, nm)^{-1}$ to about 0.7 $(cm\, nm)^{-1}$ for water at 30° C. The reference point of 30° C. is chosen because it is the approximate temperature of skin prior to irradiation. For diode and non-diode lasers, these parameters can be beneficially used to reduce the need for selecting high precision components and/or binning of lasers by wavelength.

The laser wavelength can be selected to have a thermally adjusted absorption coefficient within the range of about 8 $cm^{-1}$ to about 30 $cm^{-1}$ or within the range of about 12 $cm^{-1}$ to about 27 $cm^{-1}$. Laser wavelengths that have a thermally adjusted absorption coefficient greater than about 30 $cm^{-1}$ are more difficult to switch between semi-ablative and non-semi-ablative treatments than wavelengths with lower absorption and do not typically penetrate deeply into the tissue to be treated. Laser wavelengths that have a thermally adjusted absorption coefficient less than about 8 $cm^{-1}$ require more laser energy to switch into semi-ablative mode and are therefore less desirable.

Laser wavelengths that have a thermally adjusted absorption coefficient within the range of about 8 $cm^{-1}$ to about 30 $cm^{-1}$ provide a useful treatment depth for fractional treatment applications, particularly those that are enhanced by semi-ablative treatment. Lasers with wavelengths outside of these absorption ranges are also within the scope of the invention, particularly when coupled with other aspects of the invention, such as adjustable lens groups which can permit tight focusing of treatment beams.

The thermally adjusted absorption coefficient of a fractional laser treatment system can be chosen based on the desired treatment effect. Wavelengths that are absorbed within the tissue primarily by water are useful for treatment of wrinkles, pigmented lesions, vascular lesions, etc. For such wavelengths, the water content of the skin is important. The dermal layer of skin typically contains approximately 70% water. For a wavelength that is absorbed in the tissue primarily by water, the penetration of the light into tissue depends primarily on the absorption coefficient of the laser wavelength in water. So, for example, light with an absorption coefficient of 27 $cm^{-1}$ in water has an absorption coefficient of about 19 $cm^{-1}$ in skin, and the delivered power of a treatment beam with this absorption will be reduced by about 63% (i.e., to its 1/e point) at a depth of 0.5 mm beneath the skin surface, assuming that scattering is negligible. The actual depth of the treatment zone will depend on the exact device configuration and skin characteristics. The treatment zone depth may be deeper or shallower than the penetration depth, but will be affected by the thermally adjusted absorption coefficient. For treatment beams with a small numerical aperture, the energy deposition at a desired treatment depth can be maximized by selecting the thermally adjusted absorption coefficient in skin as approximately the inverse of the desired maximum treatment depth. For treatments where the maximum lesion depth is about 0.5 to 2 mm, the wavelength of the treatment laser can be chosen such that the thermally adjusted absorption coefficient is within the range of about 8 $cm^{-1}$ to about 30 $cm^{-1}$ or within the range of about 12 $cm^{-1}$ to about 27 $cm^{-1}$.

Figure 3:
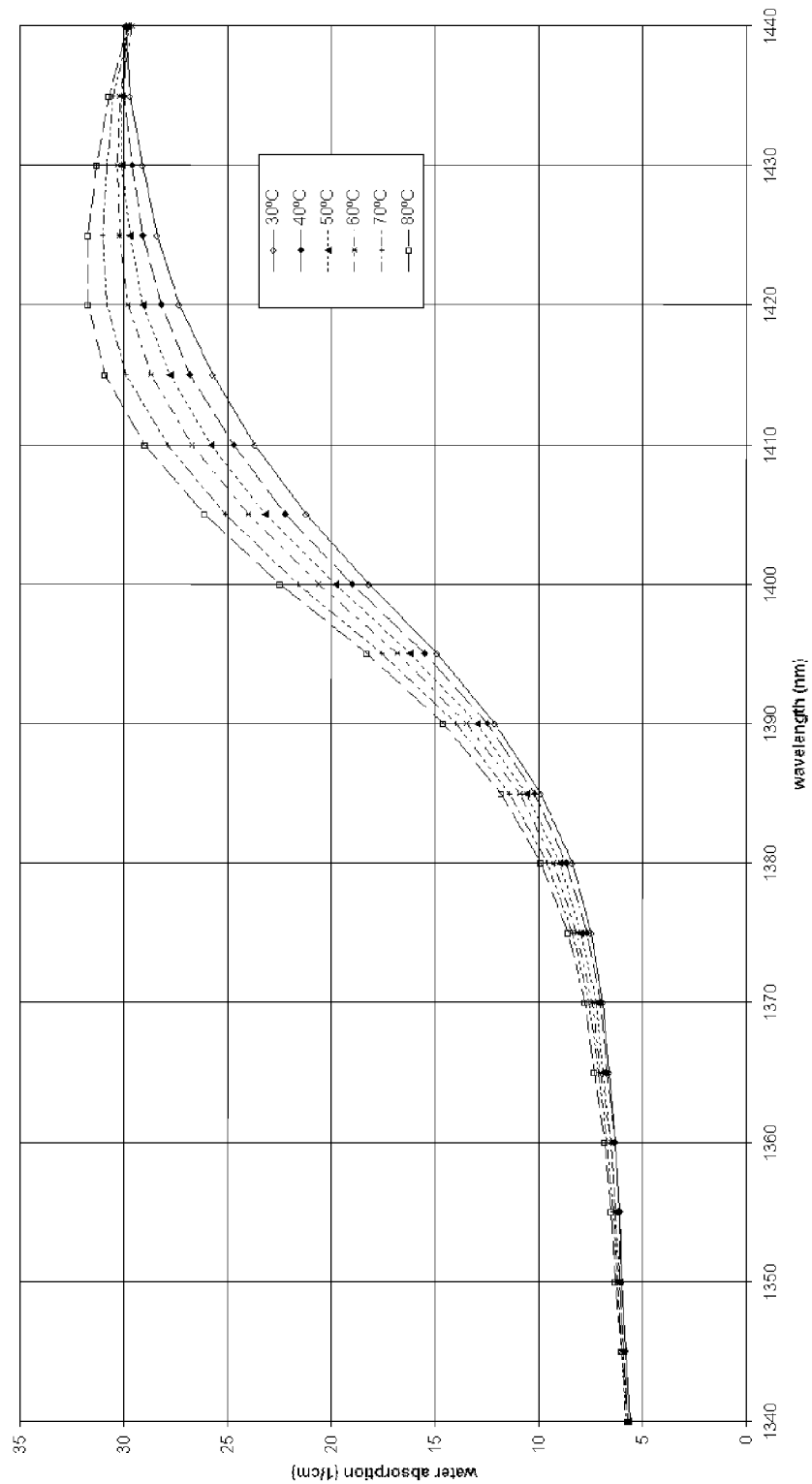
FIG. 3 is a graph showing the measured temperature dependence of the absorption spectrum of water over the temperature range of 30-80° C. for the wavelength range of 1340-1440 nm.

FIG. 3 shows measurements of the absorption spectrum for water as a function of wavelength as the temperature of water was changed from approximately 30° C. to approximately 80° C. These measurements were taken using transmission light spectroscopy, wherein light was transmitted through a heated sample of water. As the temperature of water was increased from 30° C. to 80° C., the absorption of light by water increased for light with wavelengths in the range of about 1340 nm to about 1430 nm.

As described above, the thermally adjusted absorption coefficient can be used in selecting the maximum depth of penetration for a device. The efficiency with which a treatment zone can be created to a desired depth can be further improved by adjusting the average fluence on the skin in conjunction with a choice of wavelength that has an absorption that increases dynamically as the temperature of the skin increases. For many treatments, the dynamic increase in absorption can provide important benefits to the treatment response of the skin. Some of these benefits can be illustrated with an example: For a given pulse energy, say 10 mJ, concentrating the pulse energy into a beam with a small diameter, say 30-70 µm, creates a high intensity at the treatment region and thus rapidly heats the tissue and consequently rapidly adjusts the absorption coefficient of the tissue to limit the depth of penetration. The energy in the treatment pulse is absorbed within a small depth and creates a more intense superficial local treatment effect than would occur without the dynamic change in absorption. Much of the energy of such a treatment would be absorbed within the epidermal layers of the skin and can cause a semi-ablative event. A semi-ablative treatment zone can scatter or reflect the beam to reduce the beam intensity below the upper portion of the treatment zone, which further limits the penetration of the optical treatment energy to deeper layers of tissue.

For an optical beam that is larger at the skin surface (and having the same energy, pulse duration, etc.), the rate of change in temperature at the skin surface is slower. Therefore, a larger percentage of the treatment energy can pass through the upper portions of the illuminated region when the illuminated region is at low temperature. Thus, the treatment energy can penetrate deeper into the tissue with the larger beam than for the smaller beam, particularly when the absorption dynamically increases with the temperature of the skin and/or of water within the skin. Thus, the system can function as if it has an adjustable absorption source simply by varying optical beam parameters, such as focal position, numerical aperture, beam diameter, and beam shape. This can avoid a need for employing an expensive tunable source in certain laser treatment systems.

A laser wavelength that has an absorption that increases in water with increasing temperature allows lower pulse energies to be used to create semi-ablative treatments than would be possible for wavelengths of similar absorptions at 30° C. Such wavelengths also can be beneficially incorporated with appropriate optical design to limit the depth of coagulation and damage within the dermis to prevent overtreatment.

Additionally, such dynamic absorption can be used to create a more reliable system that switches between a treatment mode that is semi-ablative and a treatment mode that is not semi-ablative. The laser wavelength can be chosen such that the absorption of the laser wavelength in water increases by at least 10% as the temperature of water is increased from 30° C. to 80° C., increases by about 10% to about 24% as the temperature of water is increased from 30° C. to 80° C., or increases by about 16% to about 24% as the temperature of water is increased from 30° C. to 80° C.

Figure 4:
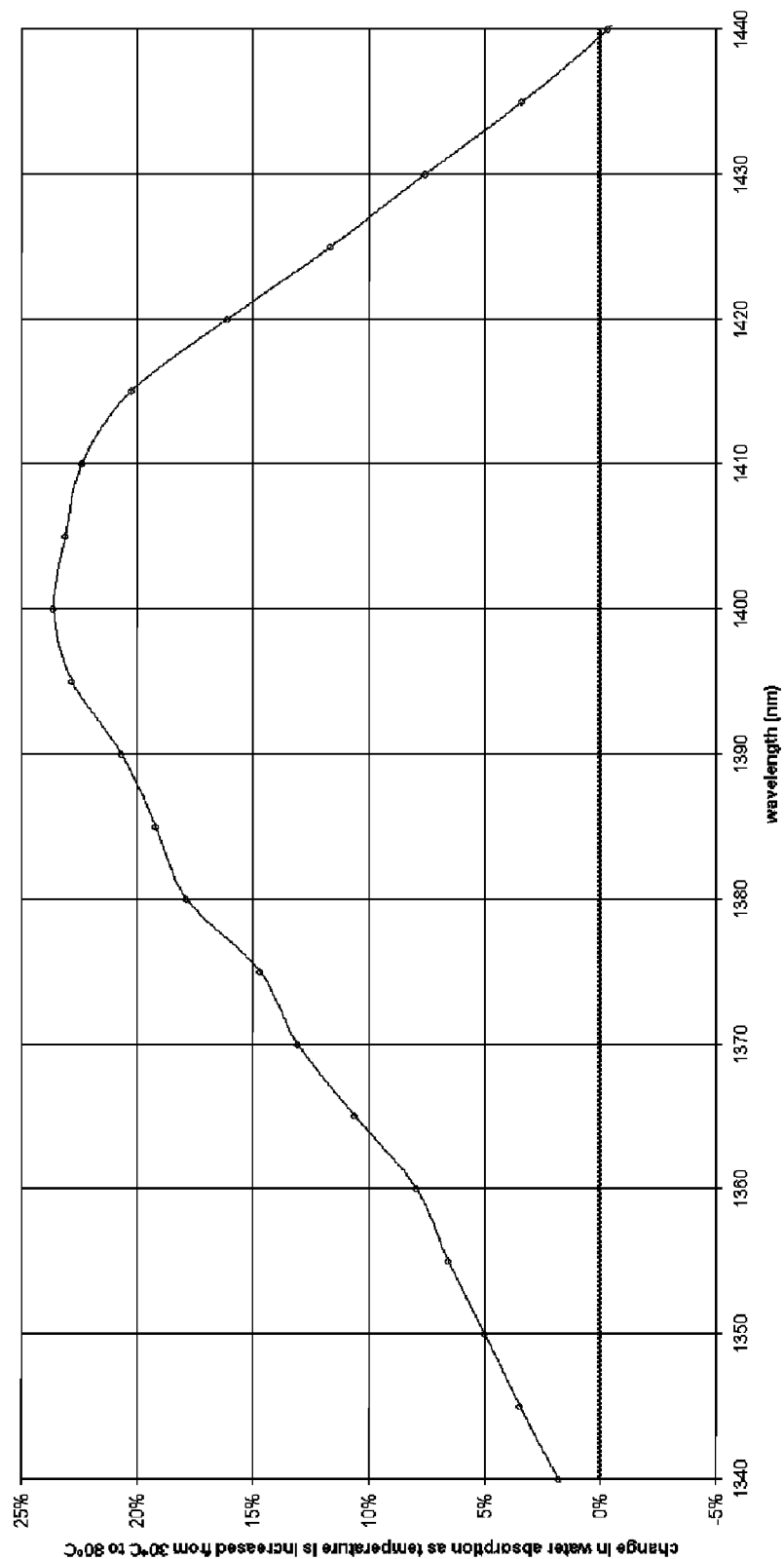
FIG. 4 is a graph showing the measured percentage difference in the absorption of water at 80° C. and absorption of water at 30° C. as a function of wavelength for the wavelength range of 1340-1440 nm.

The percentage change in absorption as water was heated from approximately 30° C. to approximately 80° C. is shown in FIG. 4. As mentioned earlier, the absorption of light by water increases with temperature over the wavelength range of about 1350 nm to about 1430 nm. The measured percentage increase in absorption was within the range of about 10% to about 24% in the wavelength range of about 1365 nm to about 1425 nm. In wavelength range of about 1380 nm to about 1420 nm, the change in absorption in water was within the range of about 16% to about 24%.

Given all of the factors described above, it can be desirable in many applications to operate a laser within the wavelength range of about 1380 nm to about 1420 nm, of about 1390 to about 1425 nm, of about 1400 to about 1420 nm, or of about 1410 nm. Diode lasers at these wavelengths are commonly available, such as from JDS Uniphase (Milpitas, Calif.) and nLight Corp. (Vancouver, Wash.).

The laser source 140 comprises one or more lasers. For example, the laser source can comprise one or more fiber lasers. Fiber lasers are desirable because of their high beam quality, precisely controlled wavelength, lack of temperature dependence, and lack of mirrors to be aligned. In particular, thulium doped glass fiber lasers can be used to produce wavelengths in the range of 1800-1930 nm. The output of ytterbium-doped glass fiber lasers can be Raman shifted to produce laser sources that emit wavelengths of about 1380 nm to about 1420 nm. Other wavelengths outside of these ranges are also accessible with these technologies as will be evident to those skilled in the art. Thulium lasers and Raman-shifted Ytterbium doped glass fiber lasers are available from IPG Photonics, Inc. (Oxford, Mass.).

As mentioned above, fiber lasers allow a more precise control of wavelength and have significantly less shift in wavelength with temperature than diode lasers. These qualities give fiber lasers an advantage over diode lasers in that it is less important to operate in a region where the absorption spectrum in water does not change rapidly as a function of wavelength. Therefore, for fiber lasers, the slope of the absorption curve at the laser wavelength as a function of wavelength is significantly less important.

Figure 7A:
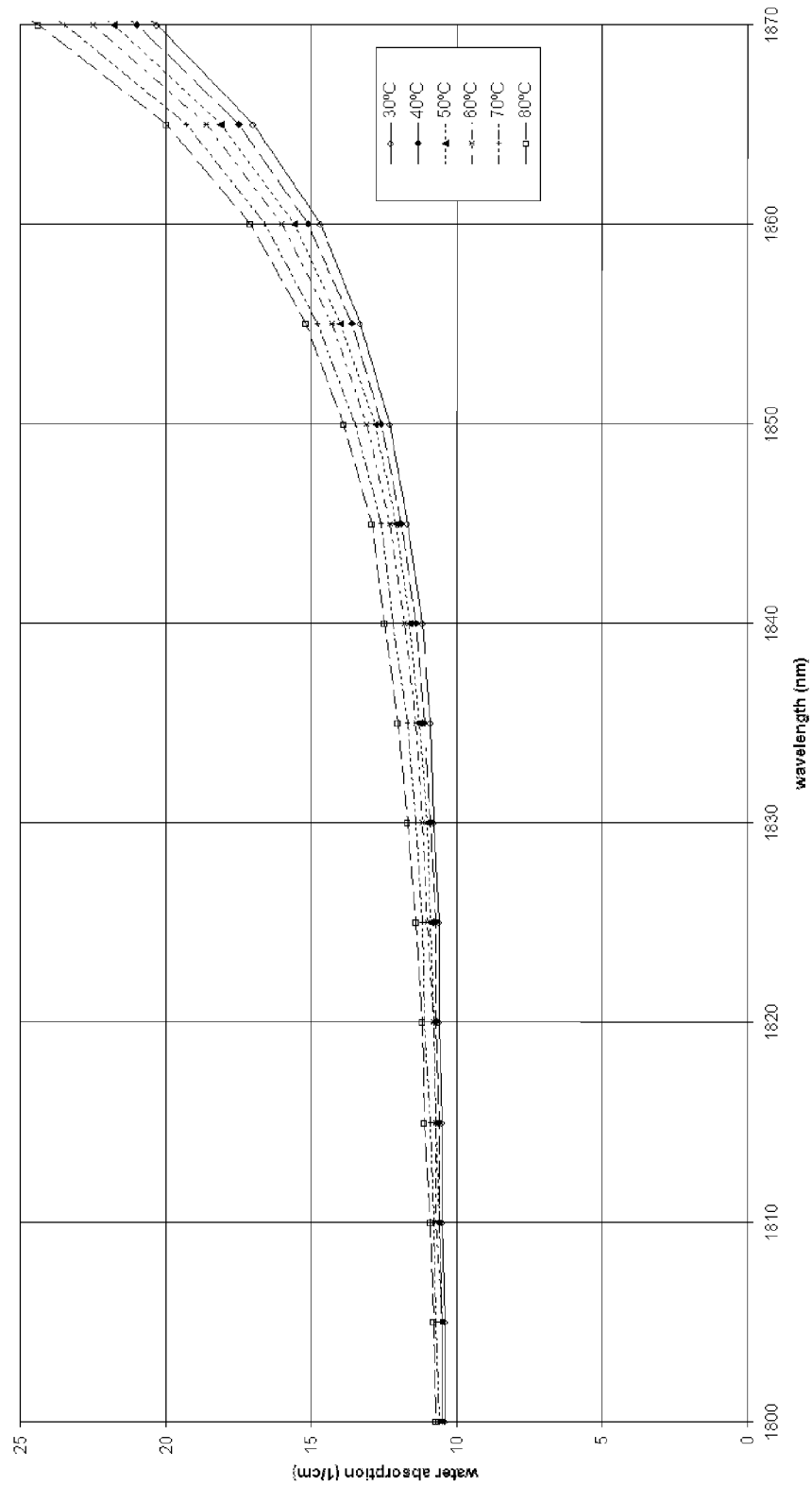
FIGS. 7A and 7B are graphs showing the measured temperature dependence of the absorption spectrum of water over the temperature range of 30-80° C. for the wavelength range of 1800-1870 nm and 1870-1930 nm, respectively.
Figure 7B:
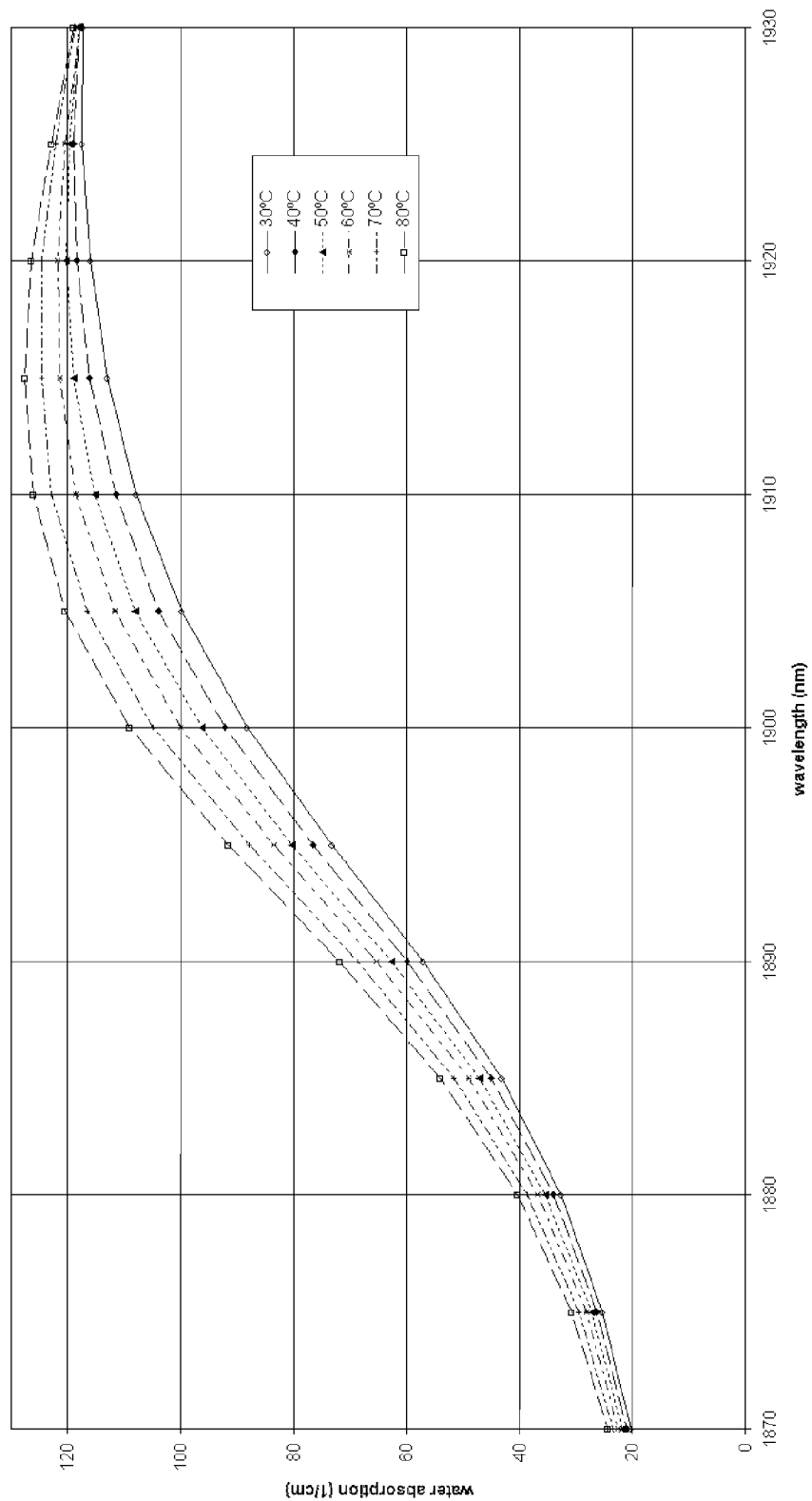

FIGS. 7A and 7B show measurements of the absorption spectrum for water as a function of wavelength as the temperature of water was changed from approximately 30° C. to approximately 80° C. These measurements were taken using transmission light spectroscopy, wherein light was transmitted through a heated sample of water. As the temperature of water was increased from 30° C. to 80° C., the absorption of light by water increased for light with wavelengths in the range of about 1800 nm to about 1930 nm.

As described above, the thermally adjusted absorption coefficient can be used in selecting the maximum depth of penetration for a device. One advantage of the wavelength range from about 1800 nm to about 1930 nm over the shorter wavelength ranges described above is that the scattering coefficients in skin are less for wavelengths within this range. This allows small beams of light that are useful for creating microscopic size treatment zones, particularly treatment zones with diameters of less than 300 μm, to be significantly deeper than they would be with the shorter wavelengths with similar absorption characteristics.

As mentioned above, by choosing a laser wavelength for which the absorption increases with temperature, the system can function as if it has an adjustable absorption source simply by varying optical beam parameters, such as focal position, numerical aperture, beam diameter, and beam shape. This can avoid a need for employing an expensive tunable source in certain laser treatment systems. For example, a single, fixed-wavelength fiber laser can be used in the laser source 140.

Figure 8:
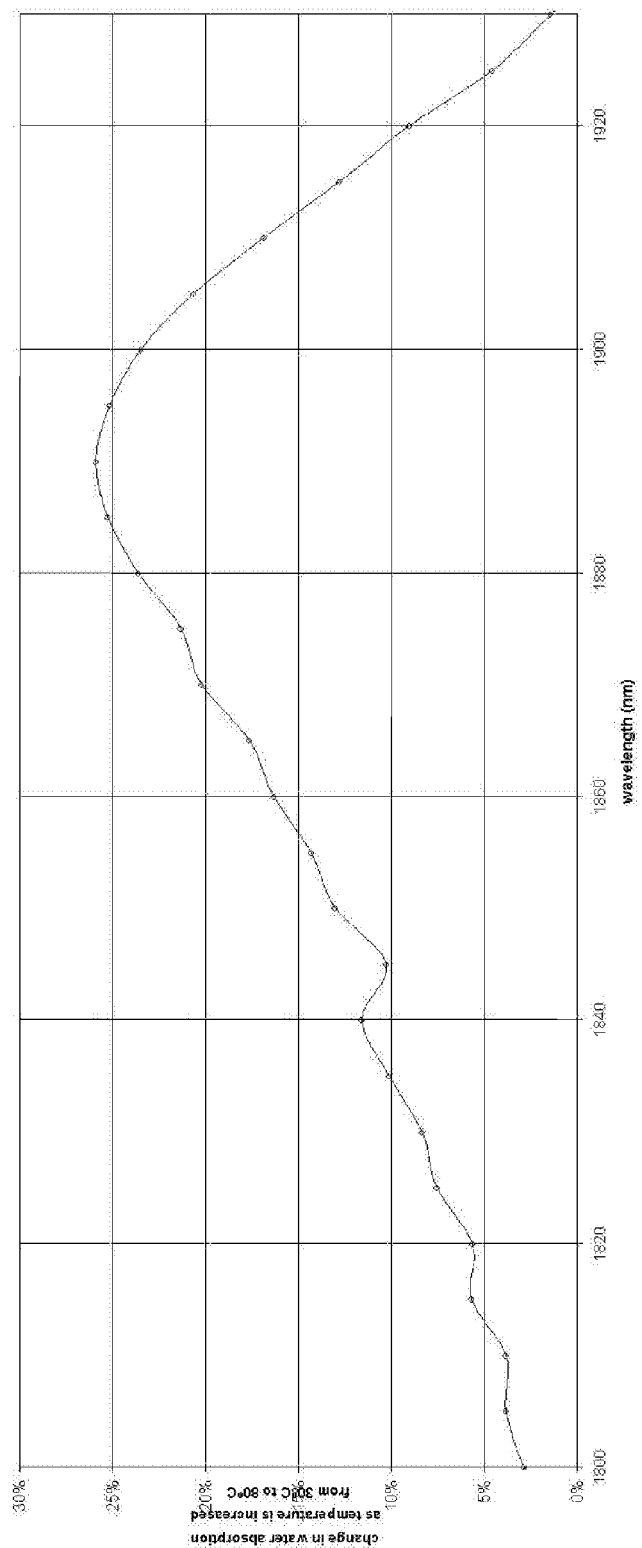
FIG. 8 is a graph showing the measured percentage difference in the absorption of water at 80° C. and absorption of water at 30° C. as a function of wavelength for the wavelength range of 1800-1930 nm.

The percentage change in absorption as water was heated from approximately 30° C. to approximately 80° C. is shown in FIG. 8. The laser wavelength can be chosen such that the absorption of the laser wavelength in water increases by about 23% to about 26% as the temperature of water is increased from 30° C. to 80° C. as in the wavelength range of about 1880 nm to about 1900 nm.

Given all of the factors described above, it can be desirable in many applications to operate a laser within the wavelength range of about 1835 nm to about 1880 nm, of about 1835 nm to about 1920 nm, or of about 1880 nm to about 1900 nm.

The adjustable lens group 123 can be adjusted during treatment or between treatments to create different optical treatment conditions resulting from changes in optical beam parameters, for example, changes in the spot size at the surface of the skin 199, the focal depth of the optical beam 130 below the surface of the skin 199, the numerical aperture of the optical beam 130 as it enters the skin 199, and or the beam cross-sectional shape at the surface of the skin 199. By adjusting the spot size, the optical treatment energy in the optical beam 130 can be concentrated or distributed to create a large or a small area of interaction between the tissue and the skin surface as desired. Small spots may be useful for creating more disruption at the surface of the skin 199. These effects can be enhanced by using a wavelength with a dynamically increasing absorption, such as wavelengths in the range of about 1390 nm to about 1425 nm. With such wavelengths, if the optical beam 130 enters the skin with a small spot size, the temperature of the upper layers of the skin will be heated rapidly and their absorption will shift quickly, thus increasing absorption and causing an increase in the local damage caused by the treatment beam. If the beam is adjusted, such that the optical beam 130 enters the skin with a large spot size, the temperature of the upper layers of the skin will be heated more slowly and their absorption will remain closer to the baseline absorption of the skin and the treatment beam will thus be able to penetrate more deeply. Large spots may also be useful for reducing the creation of bubbles of gas that might affect the focus of the optical beam 130 for larger pulse energies when deeper penetration of the optical energy is desired. Thus, by adjusting the optical beam parameters, the beam 130 can selectively switch between modes that are semi-ablative and modes that are not semi-ablative.

The treatment modes that are not semi-ablative can be further optimized to enhance the penetration depth of the treatment beam to more efficiently create treatment zones at the desired location in the skin 199 by reducing the dynamic heating in the upper layers of the skin. Various optical beam parameters can be used to vary the treatment effect of a treatment beam with dynamic absorption. For example, the use of high numerical aperture may be used to reduce or eliminate the need for cooling of the skin surface, for example, if sparing of epidermal tissue is desired.

Changing of the beam shape can be useful for minimizing the effects of visible patterns on the skin and for altering the thermal distribution within the skin to allow penetration of the beam while still maximizing concentration of the beam below the skin surface. For example, the beam may be adjusted to be more of a "flat top" shape at the skin surface to distribute the beam intensity over a larger area when deeper penetration is desired. If such a beam is then brought to a focus at the desired depth, then the heating at the desired depth can be maximized. The beam shape can alternatively be varied, for example, if one or more of lens elements 101, 102, 103 are chosen to be radially asymmetric such as for example a cylindrical element. Such radially asymmetric elements may optionally be rotated in addition to being adjusted in distance from one another in order to vary the treatment patterns. Other parameters that can be desirably varied using the inventive apparatus will be obvious to those skilled in the art.

The adjustable lens group 123 can be designed and assembled using techniques commonly employed for optical zoom lenses. For example, by appropriately adjusting the distance between two or more optical elements, the characteristics of the optical beam 130 can be adjusted.

In an embodiment, the optical spot size is focused at the skin surface for a spot size of less than approximately 90 μm. To achieve smaller spot sizes, lens elements 101 and 103 are each moved closer to lens element 102 along the optical axis. This increases the diameter of the optical beam 130 that is injected into the starburst scanner wheel 124. To achieve larger spot sizes at the surface of the skin 199, lens element 103 remains fixed and the distance between lens elements 101 and 102 is reduced as desired to move the focus of the beam into the skin 199. By moving the focus of the beam 130 into the skin 199, the diameter of the beam 130 at the surface of the skin 199 increases to distribute the optical energy over a larger area at the skin surface. Thus, the beam size and focus depth can be adjusted for the desired treatment.

Examples of ranges of appropriate optical lens design parameters are given in Table 2. Broader ranges of these parameters can be created by those skilled in the art. The specific optical design depends on the desired span for the beams, the number of spots created by the scanning wheel, the type of scanner used, the optical wavelength, and mechanical constraints of the design for the handpiece. The specific design can easily be optimized by those skilled in the art based on the constraints and desired performance for a particular system.

TABLE 2

Illustrative examples of lens design parameters

| | |
|---|---|
| Lens elements 101 and 103 | (−20)-(−15) mm focal length |
| Lens elements 102 | 10-15 mm focal length |
| Output lens group 125 | 20-50 mm focal length |
| Starburst scanner wheel 124 | diameter to outside of teeth = 40-60 mm number of teeth 15-50 |

Figure 6:
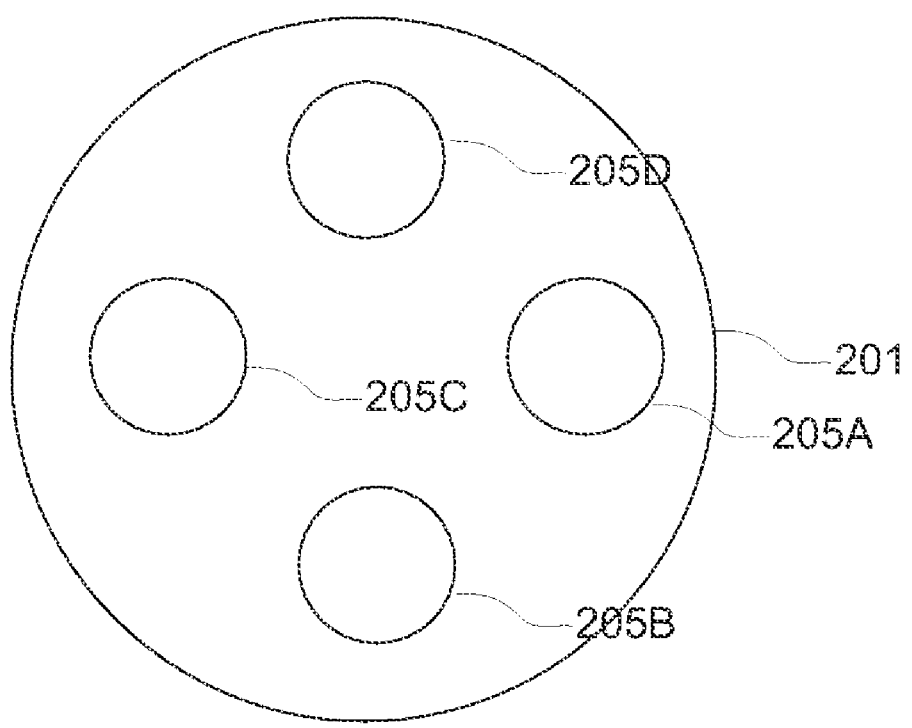
FIG. 6 is an illustration of an aspect of a fractional treatment system incorporating a rotating turret.

Other appropriate types of scanning devices can be used in this invention, such as for example, a galvanometer scanner, a piezo-electric scanner, and an acousto-optic scanner. Other appropriate types of beam adjustment devices can also be used, such as for example, other types of zoom lenses or a discretely adjustable lens variation system. One type of discretely adjustable lens variation system is illustrated in FIG. 6, which can be used to replace the adjustable lens group 123 of FIG. 1A. FIG. 6 depicts a rotating turret 201 containing discrete lenses 205A,B,C,D. Discrete lenses 205A-D may comprise a single element or a lens group. The rotating turret 205 or the adjustable lens group 123 can be manually adjusted or can be electronically adjusted, for example using a motor 182 that may optionally be controlled by a computer or other type of controller 180. The controller 180 can be accessed by the user through a user interface 184 to select appropriate treatment parameters. Through the user interface 184, the user can control the fractional optical treatment system (via the controller) to switch between a treatment mode that is semi-ablative and a treatment mode that is not semi-ablative. The controller 180 can also control parameters of the laser source such as the wavelength, pulse energy, pulse shape, pulse repetition rate, and pulse duration of an optical beam emitted from the laser source 140.

Figure 1B:
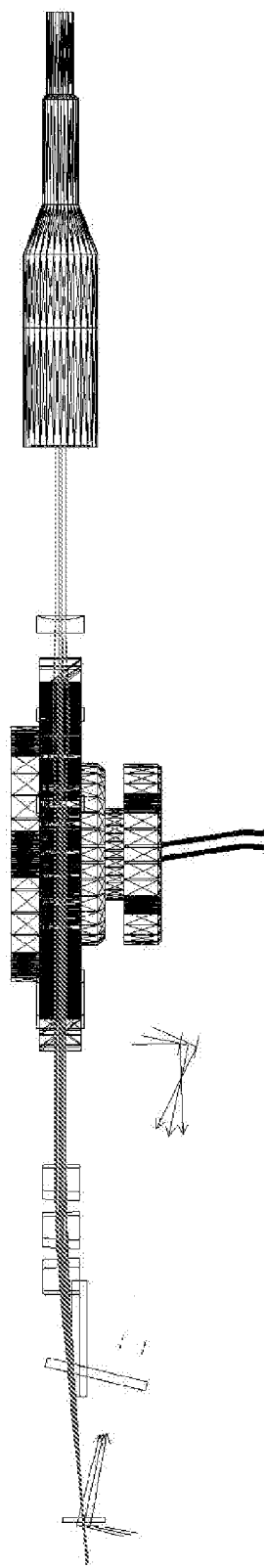
Figure 1C:
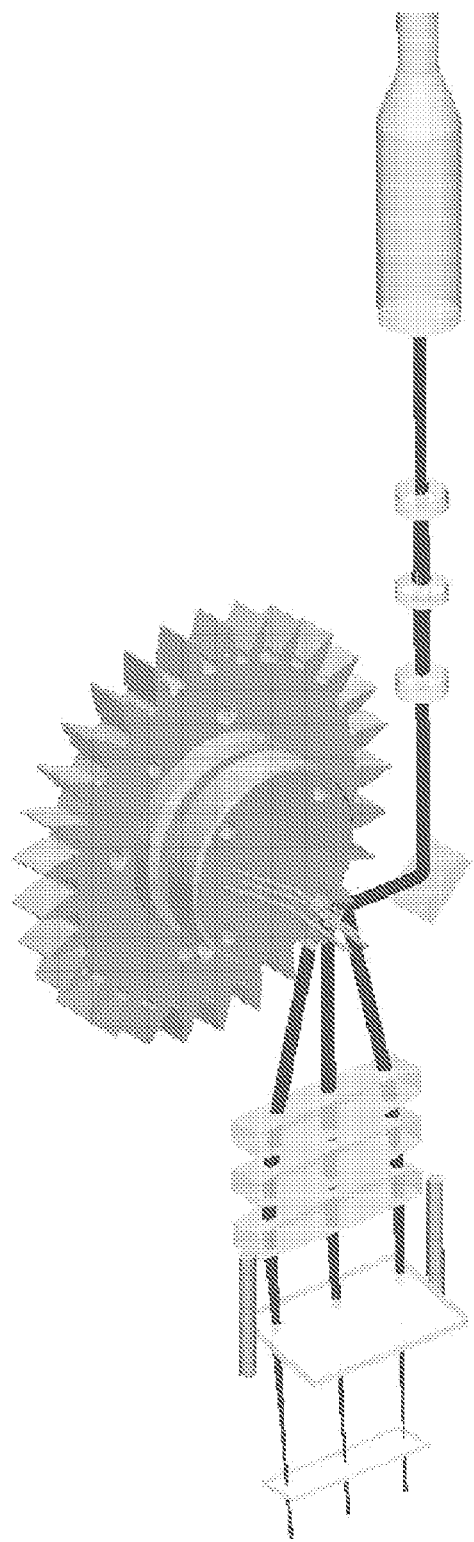

A combination of adjustment mechanisms can be incorporated for improved resolution or span. For example, FIGS. 2A-C illustrate an embodiment of the inventive apparatus that incorporates both an adjustable lens group 123 and a set of spacer tips 128A,B,C. The optical system used in FIG. 2A has a spacer tip 128A of a short length relative to the spacers used in FIGS. 2B (128B) and 2C (128C). To gain additional control over focus depth and spot size, the focus depth can be adjusted by adjusting the separation 110 between the output lens group 125 and the surface of the skin 199, where one or more beams is incident. The separation 110 can be adjusted simply, cheaply, and with no moving parts by using multiple spacer tips of different lengths that can be interchanged to achive different focus depths. FIGS. 2A-2C are illustrations of the fractional treatment system of FIG. 1A-1C that depict the use of an adjustable zoom lens in combination with a set of spacers of different lengths. This combination can beneficially be used to increase the depth of focus beyond what would be easy to do given limited space or budget constraints for the optical design of the handpiece 100.

The inventive system can comprise a noncontact tip. A noncontact tip is a tip that is designed to be in contact with the skin, but that does not have a contact element in contact with the skin (either directly or indirectly through a substance, such as a gel that is applied to the skin) in a beam path of a laser treatment beam at the point where the laser beam enters the skin. Tips that are not noncontact may have, for example, a glass or sapphire plate in the laser beam path at the point that the contact plate touches the skin. For the high optical fluences used for semi-ablative fractional treatments, high fluence levels created near the skin surface may damage a contact plate. Furthermore, tissue that is removed from the skin surface may also attach to a contact plate and cause an absorption site that causes an increased rate of damage to the contact window. Damage to a contact window may obstruct the beam and so is typically undesirable.

The inventive system can comprise a contact tip. A contact tip is a tip that is configured such that a substantially transparent contact plate is in contact with the skin during treatment and the contact plate is in contact with the skin (either directly or indirectly through a substance, such as a gel that is applied to the skin) at the point where a laser treatment beam enters the skin. Contact treatment tips can be beneficial for treatment in the treatment modes that are not semi-ablative because they allow cooling to be delivered and/or because they can allow thermal heat spreading of the heat. Thus, contact tips can reduce the increase in absorption caused by thermal heating of the upper layers of skin.

The inventive system can be sold with a set of tips that comprise one or more contact tips and one or more noncontact tips. As described above, the tips could be used to enhance the effects of dynamic absorption and optical beam parameter changes that can be used to switch treatment modes. For example, the inventive system can be sold with a set of tips that comprise a contact tip for treatments that are not semiablative and a noncontact tip for treatments that are semiablative. Whether a contact or noncontact tip is used will depend on the specific device configuration and the desired treatment outcome.

Although the detailed description contains many specifics, these should not be construed as limiting the scope of the invention but merely as illustrating different examples and aspects of the invention. It should be appreciated that the scope of the invention includes other embodiments not discussed in detail above. For example, reflective or diffractive optics may be used in place of the refractive optics described herein. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. An apparatus for fractional dermatological treatment of skin, the apparatus comprising:
    a laser source that emits optical energy at a laser wavelength, wherein the absorption of said laser wavelength in water increases as the tissue is heated from 30° C. to 80° C. and said laser wavelength is in the range of 1350 nm to 3000 nm;
    a fractional optical delivery system that delivers an optical beam emitted from said laser source to a target area of skin, said fractional optical delivery system comprising an adjustment mechanism that adjusts one or more parameters of said optical beam selected from the group consisting of a size of the optical beam at the skin surface, a focal depth of the optical beam below the skin surface, a numerical aperture of the optical beam as the optical beam enters the skin, and a beam cross-sectional shape at the skin surface; and
    a controller that electronically controls said adjustment mechanism, said controller configured to control said adjustment mechanism to switch between a semi-ablative treatment mode for a preselected pulse energy for said optical beam and a treatment mode that is non-semi-ablative for said preselected pulse energy.

2. The apparatus of claim 1 wherein said adjustment mechanism adjusts the size of the optical beam at the surface of the skin.

3. The apparatus of claim 2 wherein said adjustment mechanism is configured to adjust an optical spot size of the optical beam at the surface of the skin to at least one optical spot size within the range of about 50 µm and 120 µm wherein optical spot size is measured to the $1/e^2$ intensity level of the optical beam.

4. The apparatus of claim 1 wherein said adjustment mechanism adjusts the focal depth of the optical beam below the surface of the skin.

5. The apparatus of claim 1 wherein said adjustment mechanism adjusts the numerical aperture of the optical beam as the optical beam enters the surface of the skin.

6. The apparatus of claim 1 wherein the laser wavelength is selected with at least one of the characteristics in the group consisting of
    a thermally adjusted absorption coefficient of water in the skin is within the range of about 8 $cm^{-1}$ to about 30 $cm^{-1}$;
    a thermally adjusted absorption coefficient of water in the skin is within the range of about 12 $cm^{-1}$ to about 27 $cm^{-1}$;
    a derivative of the absorption for water at 30° C. in the skin with respect to wavelength is less than about 0.7 $(cm\ nm)^{-1}$ at the laser wavelength;
    a derivative of the absorption for water at 30° C. in the skin with respect to wavelength is within the range of about 0.3 to about 0.7 $(cm\ nm)^{-1}$ at the laser wavelength;
    the absorption of the laser wavelength by water in the skin increases by at least 10% as the temperature of water is increased from 30° C. to 80° C.;
    the absorption of the laser wavelength by water in the skin increases by about 10% to about 24% as the temperature of water is increased from 30° C. to 80° C.; and
    the absorption of the laser wavelength by water in the skin increases by about 16% to about 24% as the temperature of water is increased from 30° C. to 80° C.

7. The apparatus of claim 1 wherein the laser wavelength is selected such that a thermally adjusted absorption coefficient of water in the skin at the laser wavelength is within the range of about 8 $cm^{-1}$ to about 30 $cm^{-1}$, a derivative of the absorption for water at 30° C. in the skin with respect to wavelength is within the range of about 0.3 to about 0.7 $(cm\ nm)^{-1}$ at the laser wavelength, and the absorption of the laser wavelength by water in the skin increases by about 10% to about 24% as the temperature of the water is increased from 30° C. to 80° C.

8. The apparatus of claim 1 wherein the laser wavelength is selected such that a thermally adjusted absorption coefficient of water in the skin at the laser wavelength is within the range of about 12 $cm^{-1}$ to about 27 $cm^{-1}$, a derivative of the absorption for water at 30° C. in the skin with respect to wavelength is within the range of about 0.3 to about 0.7 $(cm\ nm)^{-1}$ at the laser wavelength, and the absorption of the laser wavelength by water in the skin increases by about 16% to about 24% as the temperature of the water is increased from 30° C. to 80° C.

9. The apparatus of claim 1 wherein the absorption of the laser wavelength by water in the skin increases by about 23% to about 26% as the temperature of water is increased from 30° C. to 80° C.

10. The apparatus of claim 1 wherein the laser wavelength is in the range of about 1390 nm to about 1425 nm.

11. The apparatus of claim 10 wherein said laser source comprises a laser diode.

12. The apparatus of claim 10 wherein said laser source comprises a Raman-shifted ytterbium-doped fiber laser.

13. The apparatus of claim 1 wherein the laser wavelength is in the range of about 1380 nm to about 1420 nm.

14. The apparatus of claim 1 wherein the laser wavelength is in the range of about 1835 nm to about 1920 nm.

15. The apparatus of claim 14 wherein said laser source comprises a thulium fiber laser.

16. The apparatus of claim 14 wherein said laser source comprises a Raman-shifted ytterbium-doped fiber laser.

17. The apparatus of claim 1 wherein said laser wavelength is in the range of about 1835 nm to about 1880 nm.

18. The apparatus of claim 1 wherein said laser wavelength is in the range of about 1880 nm to about 1900 nm.

19. The apparatus of claim 1 wherein the adjustment mechanism includes an adjustable lens group.

20. The apparatus of claim 1 wherein the adjustment mechanism includes discretely interchangeable optical elements.

21. An apparatus for fractional dermatological treatment of skin, the apparatus comprising:
    a laser source that emits optical energy at a laser wavelength, wherein the absorption of said laser wavelength in water increases as the tissue is heated from 30° C. to 80° C. and said laser wavelength is in the range of 1350 nm to 3000 nm;
    a fractional optical delivery system that delivers an optical beam emitted from said laser source to a target area of skin, said fractional optical delivery system comprising an adjustment mechanism that adjusts one or more parameters of said optical beam selected from the group consisting of a size of the optical beam at the skin surface, a focal depth of the optical beam below the skin surface, a numerical aperture of the optical beam as the optical beam enters the skin, and a beam cross-sectional shape at the skin surface; and
    a controller configured to switch the apparatus from a semi-ablative mode to a non-semi-ablative mode by adjusting an adjustable lens group and/or by exchanging interchangeable optical elements.

22. The apparatus of claim 21 wherein said laser wavelength is in the range of about 1390 nm to about 1425 nm.

23. The apparatus of claim 21 wherein the controller is configured to switch the apparatus from the semi-ablative mode to the non-semi-ablative mode by adjusting the adjustable lens group.

24. An apparatus for fractional dermatological treatment of skin, the apparatus comprising:
   a laser source that emits optical energy at a laser wavelength, wherein the absorption of said laser wavelength in water increases as the tissue is heated from 30° C. to 80° C. and said laser wavelength is in the range of 1350 nm to 3000 nm;
   a fractional optical delivery system that delivers an optical beam emitted from said laser source to a target area of skin, said fractional optical delivery system comprising an adjustment mechanism that adjusts one or more parameters of said optical beam selected from the group consisting of a size of the optical beam at the skin surface, a focal depth of the optical beam below the skin surface, a numerical aperture of the optical beam as the optical beam enters the skin, and a beam cross-sectional shape at the skin surface; and
   a user interface that selects between semi-ablative treatment parameters and non-semi-ablative treatment parameters.

25. The apparatus of claim 24 wherein said laser wavelength is in the range of about 1390 nm to about 1425 nm.

26. The apparatus of claim 24 wherein the adjustment mechanism includes an adjustable lens group.

27. The apparatus of claim 24 wherein the adjustment mechanism includes discretely interchangeable optical elements.

28. An apparatus for fractional dermatological treatment of skin, the apparatus comprising:
   a laser source that emits an optical beam at a wavelength in the range of about 1390 nm to about 1425 nm and selected from the range such that an absorption in water dynamically increases as the skin is heated from 30° C. to 80° C.;
   a fractional optical delivery system that delivers the optical beam emitted from said laser source to a treatment area on the skin, the fractional optical delivery system comprising an adjustment mechanism that adjusts the optical spot size of the optical beam at the skin, and the adjustment mechanism includes an adjustable lens group and/or discretely interchangeable optical elements; and
   a controller configured to electronically control said fractional optical delivery system to switch between a first treatment mode that is semi-ablative at a preselected pulse energy for the optical beam and a second treatment mode that is non-semi-ablative for the preselected pulse energy.

29. The apparatus of claim 28 wherein the laser wavelength is in the range of about 1400 nm to about 1420 nm.

30. The apparatus of claim 28 wherein the laser wavelength is about 1410 nm.

31. The apparatus of claim 28 further comprising:
   a noncontact tip.

32. The apparatus of claim 28 further comprising:
   a contact tip.

33. The apparatus of claim 28 further comprising:
   a set of tips comprising at least one noncontact tip and at least one contact tip.

34. An apparatus for fractional dermatological treatment of skin, the apparatus comprising:
   a laser source that emits an optical beam at a wavelength in the range of about 1390 nm to about 1425 nm and selected from the range such that an absorption in water dynamically increases as the skin is heated from 30° C. to 80° C.;
   a fractional optical delivery system that delivers the optical beam emitted from said laser source to a treatment area on the skin, the fractional optical delivery system comprising an adjustment mechanism that adjusts the optical spot size of the optical beam at the skin, and the adjustment mechanism includes an adjustable lens group and/or discretely interchangeable optical elements; and
   a controller configured to electronically switch the apparatus from a semi-ablative mode to a non-semi-ablative mode by adjusting the adjustable lens group and/or by exchanging the interchangeable optical elements.

35. The apparatus of claim 34 wherein the controller is configured to electronically switch the apparatus from the semi-ablative mode to the non-semi-ablative mode by adjusting the adjustable lens group.

36. An apparatus for fractional dermatological treatment of skin, the apparatus comprising:
   a laser source that emits an optical beam at a wavelength in the range of about 1390 nm to about 1425 nm and selected from the range such that an absorption in water dynamically increases as the skin is heated from 30° C. to 80° C.;
   a fractional optical delivery system that delivers the optical beam emitted from said laser source to a treatment area on the skin, the fractional optical delivery system comprising an adjustment mechanism that adjusts the optical spot size of the optical beam at the skin, and the adjustment mechanism includes an adjustable lens group and/or discretely interchangeable optical elements; and
   a controller that electronically controls said fractional optical delivery system; and
   a user interface coupled with the controller, the user interface configured to select between semi-ablative treatment parameters and non-semi-ablative treatment parameters.

* * * * *

UNITED STATES PATENT AND TRADEMARK OFFICE
CERTIFICATE OF CORRECTION

| | | |
|---|---|---|
| PATENT NO. | : 7,938,821 B2 | |
| APPLICATION NO. | : 11/777965 | |
| DATED | : May 10, 2011 | |
| INVENTOR(S) | : Kin F. Chan et al. | |

It is certified that error appears in the above-identified patent and that said Letters Patent is hereby corrected as shown below:

At column 15, claim 6, line 59, remove the hard return after "is".

Signed and Sealed this
Fifth Day of July, 2011

David J. Kappos
*Director of the United States Patent and Trademark Office*